United States Patent
Wang et al.

(10) Patent No.: US 8,906,300 B2
(45) Date of Patent: Dec. 9, 2014

(54) EVEN PERFUSION PUMP-INTEGRATED BLOOD OXYGENATOR

(75) Inventors: Dongfang Wang, Lexington, KY (US); Joseph B. Zwischenberger, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 82 days.

(21) Appl. No.: 13/584,704

(22) Filed: Aug. 13, 2012

(65) Prior Publication Data
US 2013/0094997 A1    Apr. 18, 2013

Related U.S. Application Data

(60) Provisional application No. 61/522,411, filed on Aug. 11, 2011, provisional application No. 61/651,164, filed on May 24, 2012.

(51) Int. Cl.
*A61M 1/00* (2006.01)
*A61M 37/00* (2006.01)

(52) U.S. Cl.
USPC .............. 422/46; 422/44; 604/6.11; 604/6.14

(58) Field of Classification Search
CPC ............ A61M 1/1698; A61M 1/3666; A61M 2001/1006; A61M 2001/1032; A61M 2001/106
USPC ..................... 422/48, 46; 604/6.11, 6.13, 6.14
See application file for complete search history.

(56) References Cited

U.S. PATENT DOCUMENTS

| | | | |
|---|---|---|---|
| 973,868 A | 10/1910 | Kneuper | |
| 2,474,665 A | 6/1949 | Guarino | |
| 2,742,158 A | 4/1956 | Schuller | |
| 3,103,928 A | 9/1963 | Broman | |
| 3,183,908 A | 5/1965 | Collins et al. | |
| 3,410,263 A | 11/1968 | McGinnis | |
| 3,429,443 A | 2/1969 | Stern | |
| 3,768,977 A | 10/1973 | Brumfield et al. | |
| 3,855,995 A | 12/1974 | Bentley | |
| 3,856,475 A | 12/1974 | Marx | |
| 3,898,045 A | 8/1975 | Bowley | |
| 3,934,982 A | 1/1976 | Arp | |
| 3,935,110 A | 1/1976 | Schmid et al. | |
| 3,960,657 A | 6/1976 | Bowley | |
| 3,989,626 A * | 11/1976 | Bentley et al. | 210/177 |
| 4,017,279 A | 4/1977 | Bowley | |
| 4,094,792 A | 6/1978 | Bentley | |
| 4,098,275 A | 7/1978 | Consalvo | |
| 4,134,402 A | 1/1979 | Mahurkar | |
| 4,188,360 A | 2/1980 | Kurata | |
| 4,196,075 A | 4/1980 | Bentley | |
| 4,205,042 A | 5/1980 | Lobdell et al. | |
| 4,268,476 A | 5/1981 | Raible | |
| 4,297,318 A | 10/1981 | Raible | |
| 4,368,118 A | 1/1983 | Siposs | |
| 4,372,914 A | 2/1983 | Raible | |
| 4,374,088 A | 2/1983 | Stenberg et al. | |
| 4,533,516 A | 8/1985 | Johnsson et al. | |

(Continued)

*Primary Examiner* — Leslie Deak
(74) *Attorney, Agent, or Firm* — King & Schickli, PLLC

(57) ABSTRACT

A blood oxygenator includes an integral pneumatic pump disposed substantially within a housing thereof, an inlet blood flow redirector, and an outflow blood collector. An atrium provided at an inlet of the oxygenator promotes even delivery of blood to the oxygenator. In use, the oxygenator provides an even dispersion of blood therethrough, establishing even perfusion and reducing areas of stagnant blood flow.

9 Claims, 11 Drawing Sheets

(56) References Cited

U.S. PATENT DOCUMENTS

| | | | |
|---|---|---|---|
| 4,552,552 | A * | 11/1985 | Polaschegg et al. ......... 604/6.05 |
| 4,573,883 | A | 3/1986 | Noon et al. |
| 4,612,126 | A | 9/1986 | Alt et al. |
| 4,623,518 | A | 11/1986 | Raible |
| 4,698,207 | A | 10/1987 | Bringham et al. |
| 4,770,652 | A | 9/1988 | Mahurkar |
| 4,808,155 | A | 2/1989 | Mahurkar |
| 4,874,581 | A | 10/1989 | Sutherland et al. |
| 4,906,229 | A | 3/1990 | Wampler |
| 4,908,014 | A | 3/1990 | Kroyer |
| 4,915,837 | A | 4/1990 | Verity |
| 4,925,377 | A | 5/1990 | Inacio et al. |
| 4,975,247 | A | 12/1990 | Badolato et al. |
| 5,034,188 | A | 7/1991 | Nakanishi et al. |
| RE33,932 | E | 5/1992 | Fukasawa et al. |
| 5,116,308 | A | 5/1992 | Hagiwara |
| 5,120,501 | A | 6/1992 | Mathewson et al. |
| 5,139,741 | A | 8/1992 | Hagiwara |
| 5,158,533 | A | 10/1992 | Strauss et al. |
| 5,188,732 | A | 2/1993 | De Niel et al. |
| 5,197,951 | A | 3/1993 | Mahurkar |
| 5,217,689 | A | 6/1993 | Raible |
| 5,221,255 | A | 6/1993 | Mahurkar et al. |
| 5,225,161 | A | 7/1993 | Mathewson et al. |
| 5,236,665 | A | 8/1993 | Mathewson et al. |
| 5,270,004 | A | 12/1993 | Cosentino et al. |
| 5,270,005 | A | 12/1993 | Raible |
| 5,282,783 | A | 2/1994 | Lindsay |
| 5,316,724 | A | 5/1994 | Mathewson et al. |
| 5,338,512 | A | 8/1994 | Mathewson et al. |
| 5,354,277 | A | 10/1994 | Guzman et al. |
| 5,358,689 | A | 10/1994 | Jones et al. |
| 5,374,245 | A | 12/1994 | Mahurkar |
| 5,395,525 | A | 3/1995 | Takano et al. |
| 5,421,405 | A | 6/1995 | Goodin et al. |
| 5,476,444 | A | 12/1995 | Keeling et al. |
| 5,718,871 | A | 2/1998 | Elgas |
| 5,762,868 | A | 6/1998 | Leonard |
| 5,762,875 | A | 6/1998 | Gremel et al. |
| 5,770,149 | A | 6/1998 | Raible |
| 5,787,729 | A | 8/1998 | Wijaya |
| 5,788,287 | A | 8/1998 | Gremel |
| 5,817,279 | A | 10/1998 | Eilers et al. |
| 5,823,987 | A * | 10/1998 | Elgas et al. ................. 604/6.13 |
| 5,858,233 | A | 1/1999 | Elgas et al. |
| 5,906,741 | A | 5/1999 | Elgas et al. |
| 5,922,202 | A | 7/1999 | Elgas et al. |
| 5,958,255 | A | 9/1999 | Hobrecht et al. |
| 6,017,493 | A | 1/2000 | Cambron et al. |
| 6,224,829 | B1 | 5/2001 | Piplani et al. |
| 6,336,911 | B1 | 1/2002 | Westerbeck |
| 6,368,557 | B1 | 4/2002 | Piplani et al. |
| 6,379,618 | B1 | 4/2002 | Piplani et al. |
| 6,395,226 | B1 | 5/2002 | Plunkett |
| 6,406,452 | B1 | 6/2002 | Westerbeck |
| 6,413,233 | B1 | 7/2002 | Sites et al. |
| 6,428,747 | B1 | 8/2002 | Dueri et al. |
| 6,454,999 | B1 | 9/2002 | Farhangnia et al. |
| 6,497,841 | B1 | 12/2002 | Plotkin et al. |
| 6,503,450 | B1 | 1/2003 | Afzal et al. |
| 6,508,983 | B1 | 1/2003 | McBurney et al. |
| 6,572,821 | B2 | 6/2003 | Knott |
| 6,579,496 | B1 | 6/2003 | Fausset et al. |
| 6,613,008 | B2 | 9/2003 | Aboul-Hosn et al. |
| 6,630,107 | B1 | 10/2003 | Merce Vives |
| 6,644,320 | B2 | 11/2003 | Groth et al. |
| 6,669,661 | B1 | 12/2003 | Yee |
| 6,682,698 | B2 * | 1/2004 | Chambers et al. .............. 422/45 |
| 6,689,315 | B2 | 2/2004 | Linker et al. |
| 6,716,157 | B2 | 4/2004 | Goldowsky |
| 6,716,188 | B2 | 4/2004 | Noda et al. |
| 6,723,283 | B2 | 4/2004 | Ghelli et al. |
| 6,726,653 | B2 | 4/2004 | Noda et al. |
| 6,730,267 | B2 | 5/2004 | Stringer et al. |
| 6,884,360 | B2 | 4/2005 | Chang |
| 6,908,446 | B2 | 6/2005 | Yokoyama et al. |
| 6,960,322 | B2 | 11/2005 | Stringer et al. |
| 7,022,099 | B2 | 4/2006 | Litzie et al. |
| 7,022,284 | B2 | 4/2006 | Brian et al. |
| 7,135,008 | B2 | 11/2006 | O'Mahony et al. |
| 7,238,320 | B2 | 7/2007 | Ghelli et al. |
| 7,541,000 | B2 | 6/2009 | Stringer et al. |
| 7,785,247 | B2 | 8/2010 | Tatum et al. |
| 2004/0226868 | A1 | 11/2004 | Shoji et al. |
| 2006/0009728 | A1 | 1/2006 | Litzie et al. |
| 2006/0177343 | A1 | 8/2006 | Brian, III et al. |
| 2007/0217948 | A1 | 9/2007 | Ghelli et al. |
| 2007/0249888 | A1 | 10/2007 | Wu et al. |
| 2008/0199357 | A1 | 8/2008 | Gellman et al. |
| 2008/0234623 | A1 | 9/2008 | Strauss et al. |
| 2010/0106072 | A1 * | 4/2010 | Kashefi-Khorasani et al. ............... 604/5.04 |
| 2013/0004369 | A1 * | 1/2013 | Marseille ................. 422/48 |

* cited by examiner

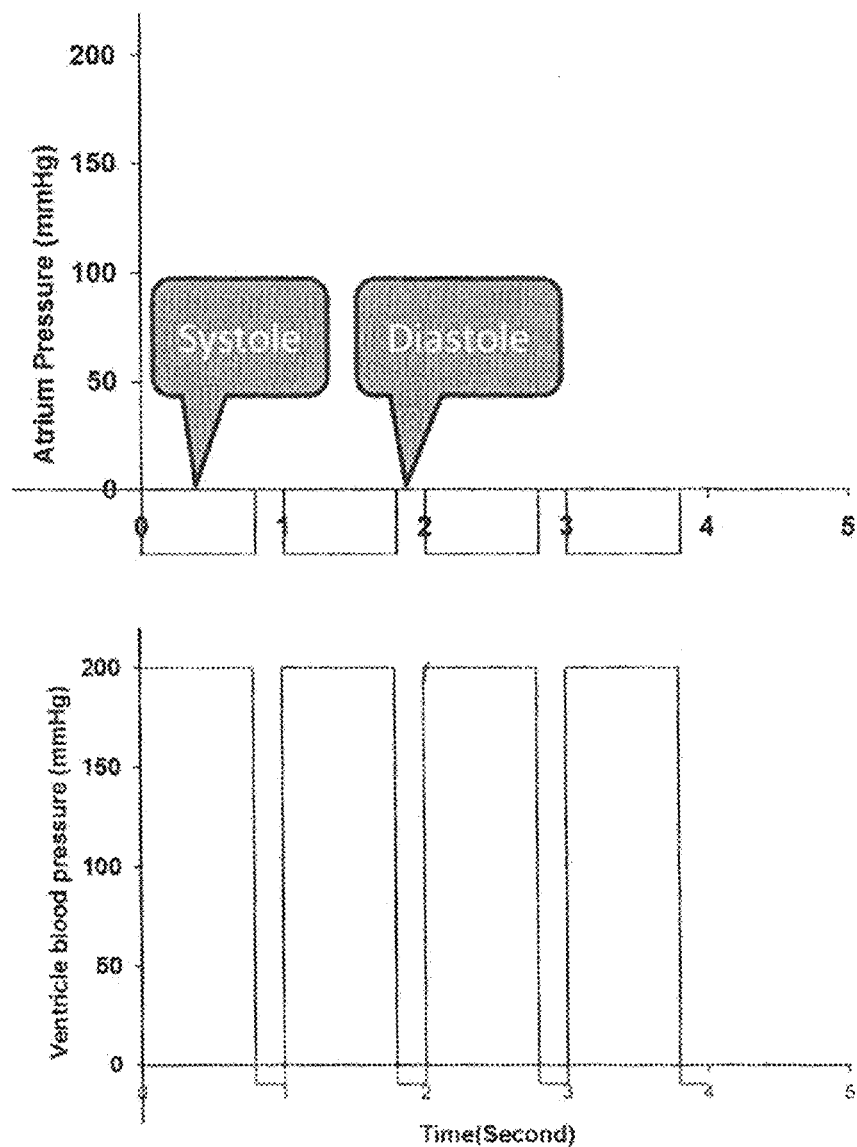

EVEN PERFUSION PUMP-INTEGRATED BLOOD OXYGENATOR

This application claims the benefit of priority in U.S. Provisional Patent Application Ser. Nos. 61/522,411 filed on Aug. 11, 2011 and 61/651,164 filed on May 24, 2012, the entirety of the disclosures of each of which are incorporated herein by reference.

TECHNICAL FIELD

The present invention relates generally to the field of medical devices. In particular, the invention relates to a pump-integrated blood oxygenator for use in artificial lung (AL) applications.

BACKGROUND OF THE INVENTION

Conventional artificial lung/gas exchanger/oxygenators include at least a body, often defining a cylinder, a blood inlet, one or more blood outlets, and a gas (oxygen) supply inlet and outlet. The interior of such devices includes a plurality of hollow membrane fibers whose porosity allows passage of gases such as oxygen and $CO_2$, but not of liquid, blood cells, blood proteins, etc. Gas inflow/outflow ports are provided, typically in fluid communication with one another via the lumens of the hollow membrane fibers, Using one or more pumps or potentially the patient's own heart pumping action, blood flow is established whereby oxygen-depleted and $CO_2$-enriched blood is removed from a patient's bloodstream, passes into the device via the blood inlet, passes over exterior surfaces of the hollow membrane fibers, and exits the device through the blood outlet. During this traversal, oxygen passes from the hollow fiber lumens into the blood, and $CO_2$ is removed from the blood and passes into the hollow fiber lumens to be removed by a sweep gas. From there, the oxygenated blood is returned to the patients bloodstream. It is for that reason that such devices are often termed "artificial lungs," for their ability to replace or supplement the gas exchange function of the patient's own lungs.

Disadvantageously, conventional artificial lungs often provide uneven blood perfusion. This is because existing such devices typically include areas wherein blood flow becomes lessened or even stagnant. This causes thrombosis and in extreme cases device failure. In turn, a traditional artificial lung circuit consists of an oxygenator/artificial lung as described for gas exchange/oxygenation, a double lumen cannula or two separate cannulas for blood infusion/drainage into/from a patient, and a blood pump to drive the blood through the circuit. In a typical pneumatically driven pump, each pumping cycle includes a systolic phase (pushing blood from a pump blood chamber into a patient through an infusion cannula lumen) and a diastolic phrase (withdrawing blood from the patient into the pump blood chamber through a drainage cannula lumen). The systolic and diastolic phases of the pumping cycle are performed alternately, not simultaneously. Therefore, the infusion/drainage cannulae can only move blood during 50% of the pumping cycle. This requires twice the blood flow rate and twice the driven pressure/delta p to move the same amount of blood compared to a pump cycle where the systolic and diastolic phases could be performed simultaneously. For this reason, a relatively larger-sized cannula is needed to move the same amount of blood as would be possible if the cannulae could move blood for a greater percentage of the pumping cycle, which is disadvantageous in situations requiring peripheral cannulation, since the cannula size is strictly limited by the size of the blood vessel to be cannulated.

To solve this and other problems, the present disclosure provides a compact hollow fiber membrane blood oxygenator including an integral pneumatic pump and blood flow redirector structures, eliminating the need for a separate pump and so simplifying the artificial lung circuit. The present disclosure also provides such an oxygenator including an additional pneumatic pump serving as an atrium, to the oxygenator pump inlet, allowing withdrawal from and pumping blood to a patient to occur simultaneously, increasing efficiency of the artificial lung circuit and the infusion/drainage cannulae, and allowing use of cannulae having a reduced inner diameter compared to conventional cannulae. The device of the present disclosure provides an even blood flow pattern, preventing or reducing incidence of thrombosis. In turn, the presently disclosed design simplifies the blood circuit and also provides a pulsatile blood flow pattern, promoting active blood mixing and thereby improving gas exchange within the pump. The present device finds use at least in treatment of acute or chronic lung failure, as well as for combined right heart and lung (RVAD) failure.

SUMMARY OF THE INVENTION

The present disclosure provides a blood oxygenator for use as an artificial lung, in RVAD, and the like. The oxygenator includes an integral pneumatic pump enclosed substantially within a housing thereof, providing a compact and efficient design. Inlet blood redirectors and outlet blood collectors are provided, which in combination with the integral pneumatic pump promote an even perfusion of blood, eliminating areas of stagnation.

In an embodiment, an atrium is provided at an inlet of the blood oxygenator. The atrium is defined by an additional pneumatic pump for promoting blood withdrawal from a patient body into the oxygenator by establishing a negative blood pressure. In this embodiment, the oxygenator pump described above functions substantially as a ventricle. The atrium pump and oxygenator pump are separately driven. During the bulk of the pumping cycle (for example, 80-95%), a positive pressure is applied to the oxygenator pump (ventricle) to push blood into the patient via an infusion cannula and a simultaneous small negative pressure applied to the atrium withdraws blood from the patient via a drainage cannula. For the remainder of the pumping cycle (in the example, 5-20%), a negative pressure is applied to the oxygenator pump (ventricle) and zero pressure is applied to the atrium, moving blood rapidly from the atrium to the ventricle By cyclically maintaining an internal pressure of the atrium pneumatic pump(s) at zero or less, a constant, even supply of blood from the patient is provided at the blood oxygenator inlet, thereby eliminating the pulsatile inlet blood flow patterns provided by conventional pumping systems.

In turn, a blood oxygenating system employing the blood oxygenator of the present disclosure is described, for removing blood from a patient body and returning blood to same.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims. Unless otherwise indicated, any references discussed herein are specifically incorporated by reference in their entirety into the present disclosure.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 11 graphically presents relative internal pressures of the atrium and oxygenator in systolic and diastolic phases.

DETAILED DESCRIPTION OF THE ILLUSTRATED EMBODIMENTS

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention. Also, it is to be understood that other embodiments may be utilized and that process, reagent, software, and/or other changes may be made without departing from the scope of the present invention.

Figure 1:
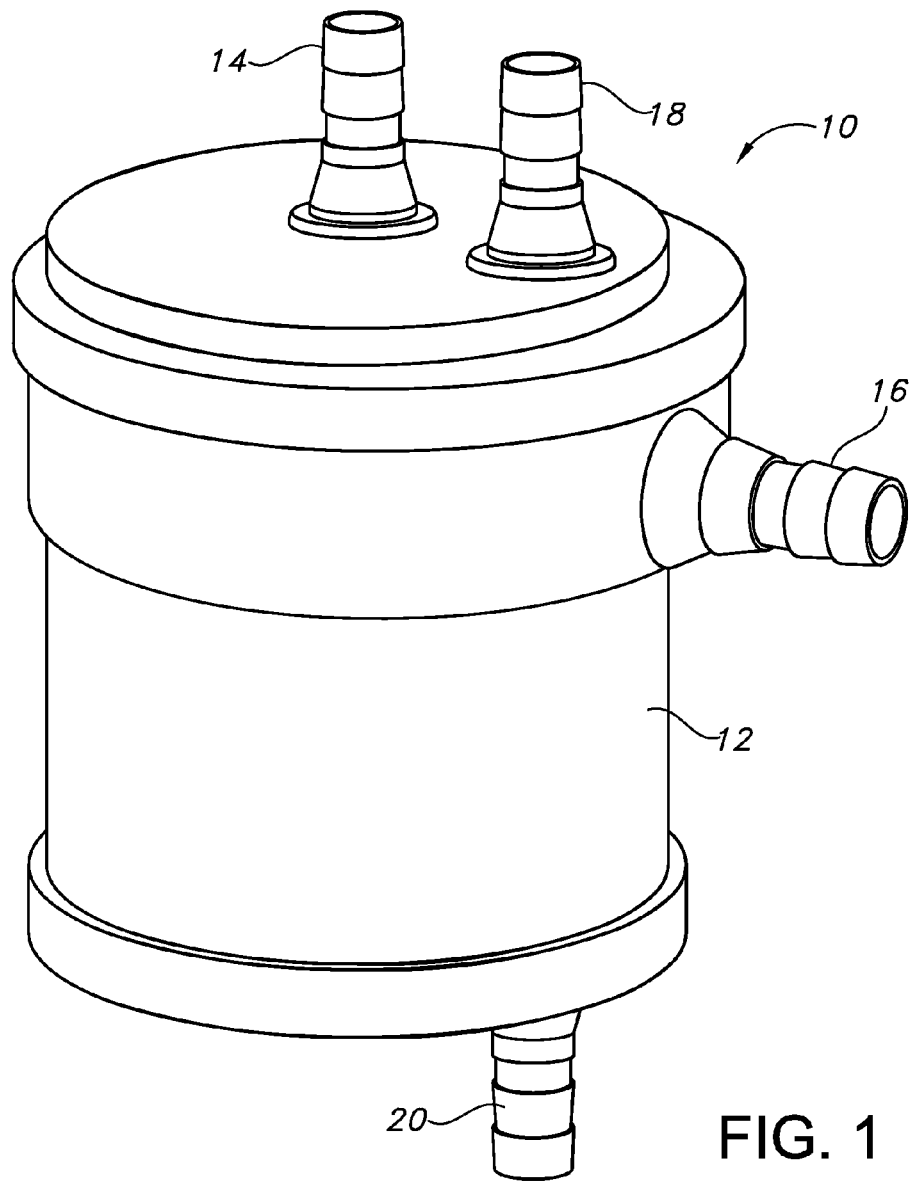
FIG. 1 shows a housing for the oxygenator of the present disclosure.

In one aspect, the present disclosure provides a blood oxygenator 10 (see FIG. 1) including a housing 12, at least one blood inlet 14. and at least one blood outlet 16. At least one sweep gas inlet 18 and at least one sweep gas outlet 20 are provided for supplying a gas to and removing same from the oxygenator 10, typically with the sweep gas being passed through the oxygenator 10 in a direction opposite that of the blood flow. For as exchange, a hollow fiber membrane array 22 is provided, using membranes as are known in the art. Arrays 22 of membranes may be provided arranged substantially parallel to a longitudinal axis of the oxygenator 10 housing 12, or alternatively diagonal spirally wound membrane arrays 22 (FIG. 2) may be provided. Each such structure is well known in the art. Inlet potting 24 and outlet potting 26 are provided and disposed to prevent entry of blood into the lumens of the hollow fibers of the membrane arrays 22, also as are known in the art. The inlet potting 24 may define an inverted dome shape, further assisting in promoting even redistribution of blood passing through the oxygenator 10.

Figure 3:
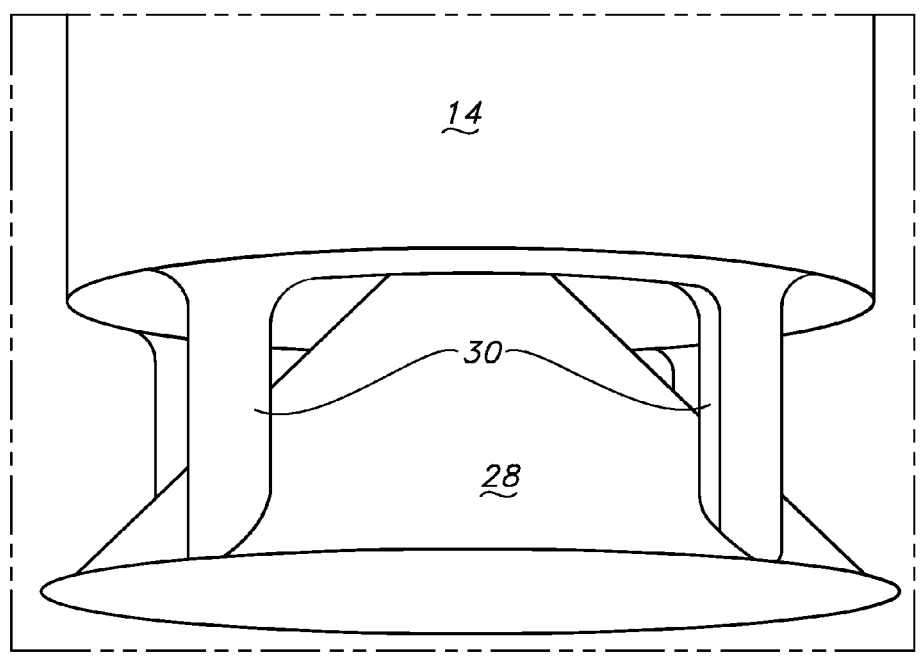
FIG. 3 shows an inlet blood flow redirector for the oxygenator.
Figure 4:
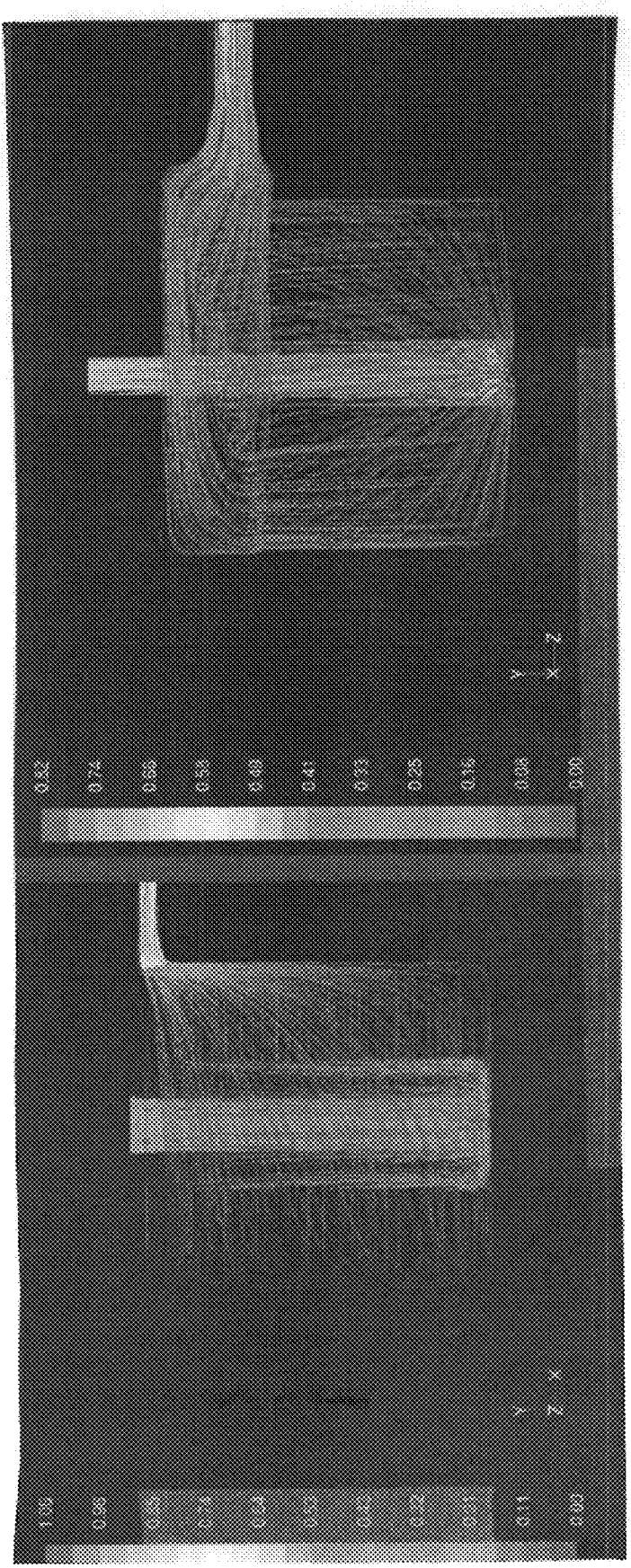
FIG. 4 graphically shows blood flow through the present oxygenator (right figure) versus a conventional oxygenator (left figure)
Figure 5:
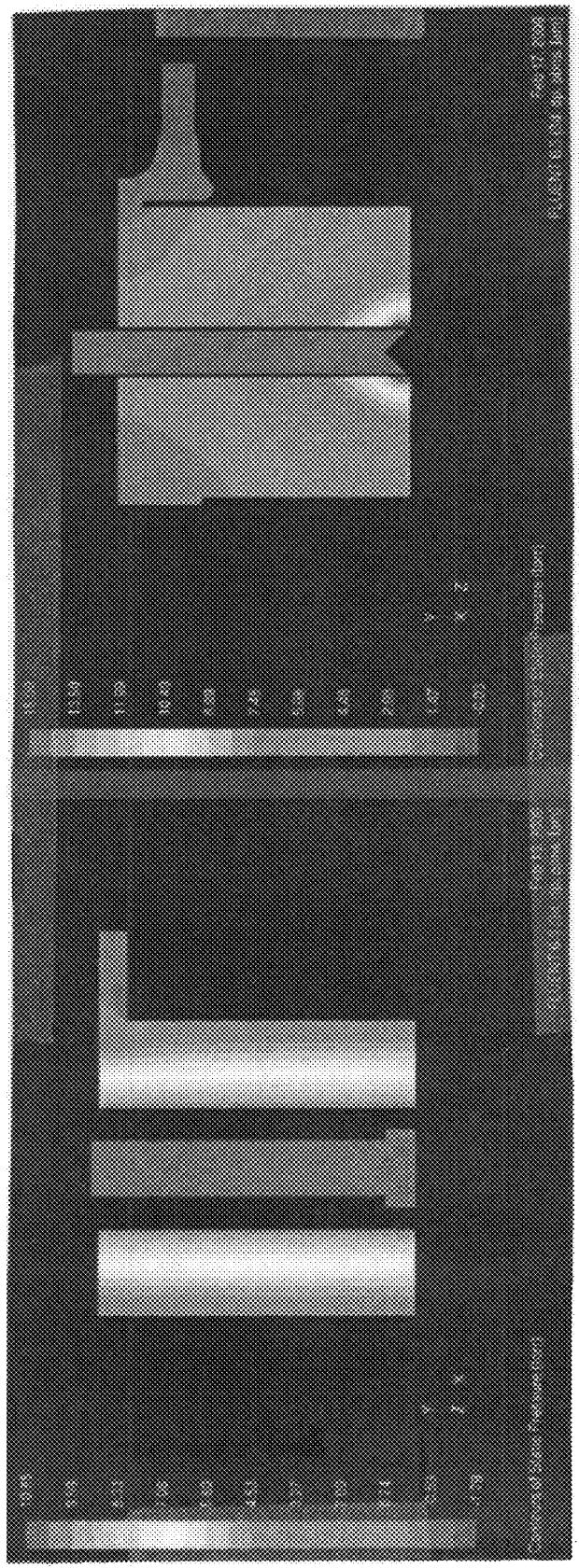
FIG. 5 shows graphically shows blood flow pressure contours for the present oxygenator (right figure) versus a conventional oxygenator (left figure)

The system 10 of the invention further includes blood flow redirector structures, providing an even blood flow pattern as blood passes through the oxygenator 10. An inlet blood flow redirector 28 is provided at an end of the oxygenator 10 distal from the blood inlet 14 for evenly redirecting blood flow passing through the blood inlet 14. In an embodiment, a frusto-conical inlet blood flow redirector 28 is provided at a distal end of the blood inlet 14 (see FIG. 3), secured to or molded with the distal end of the blood inlet 14 by one or more columns 30. At least a portion of the conical inlet blood flow redirector 28 is disposed in an interior of the blood inlet 14 distal end. Like structures are described in copending U.S. Published Patent Appl. No. 2013/0211483, filed concurrently herewith and incorporated herein in its entirety by reference.

Figure 2:
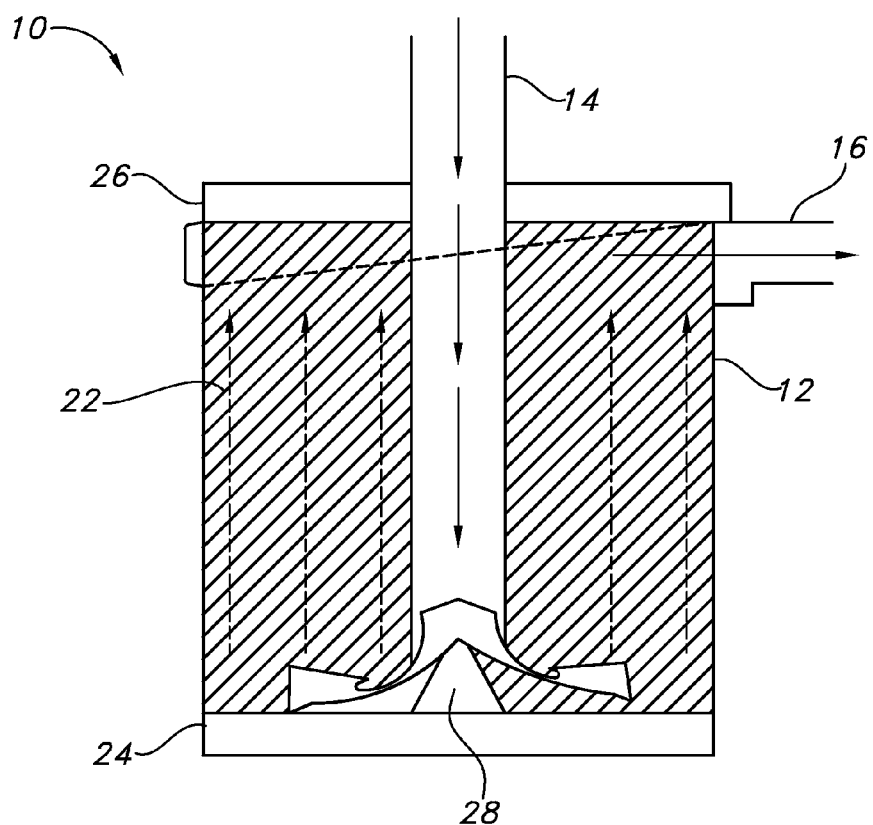
FIG. 2 shows a cross-sectional side view of the oxygenator.

As shown in FIG. 2, the inlet blood flow redirector 28 promotes even radial perfusion across a surface of the inlet potting 24 at a bottom of the oxygenator and also even axial blood flow as blood travels through the oxygenator 10 towards the blood outlet 16 (see arrows), eliminating stagnant blood flow in the oxygenator 10.

Figure 6:
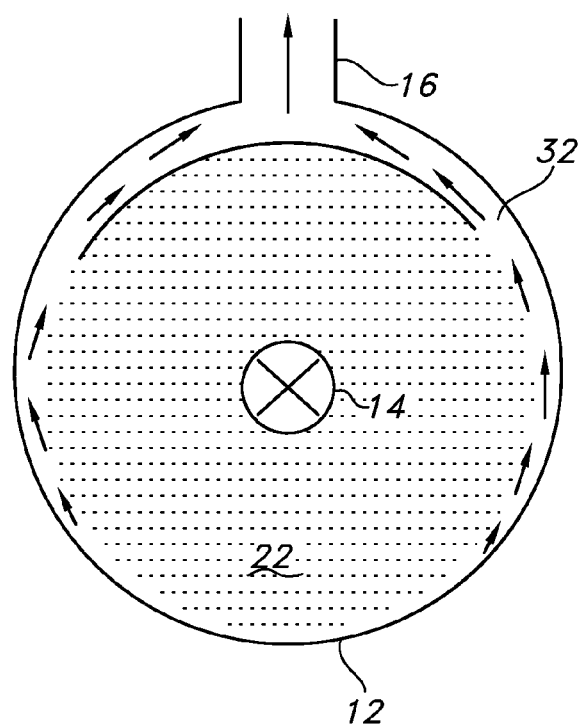
FIG. 6 shows a top view of the oxygenator of the disclosure.

In turn, a blood collection channel 32 is provided at atop of the oxygenator 10, whereby blood exiting the membrane array 22 is collected and redirected to the blood outlet 16 (see FIG. 6). A substantially crescent-shaped blood collection channel 32 is shown, although the skilled artisan will appreciate that other cross-sectional shapes are possible and contemplated, such as segmental, triangular, etc. The blood collection channel 32 regulates blood flow evenly at the outlet end of the oxygenator 10, and further guides blood to the blood outlet 16. That is, blood enters via the blood inlet 14 and is evenly redirected by the inlet blood flow redirector 28 as summarized above to pass over the hollow fiber membrane array 22. On exiting the membrane array 22, blood passes into the blood collection channel 32 and therefrom exits the oxygenator 10 via the blood outlet 16. In that manner, areas of stagnant blood flow at or near the blood outlet 16 are reduced or eliminated.

Rather than utilizing an external pump as is common with conventional oxygenators, the oxygenator 10 of the present disclosure includes an integral pneumatic pump to provide pumping action for passing blood from the blood inlet 14, over the hollow membrane array 22, and to the blood outlet 16. As such, a compact, economical and efficient combination of pump and oxygenator is provided. Providing further advantages, the integral pneumatic pump provides a pulsatile blood flow pattern, promoting active blood mixing for improved gas exchange performance and an improved blood flow pattern to reduce thrombogenicity. Because of that improved gas exchange performance, it is possible to provide a lesser gas exchange surface area compared to conventional oxygenators, allowing a more compact unit.

Figure 7:
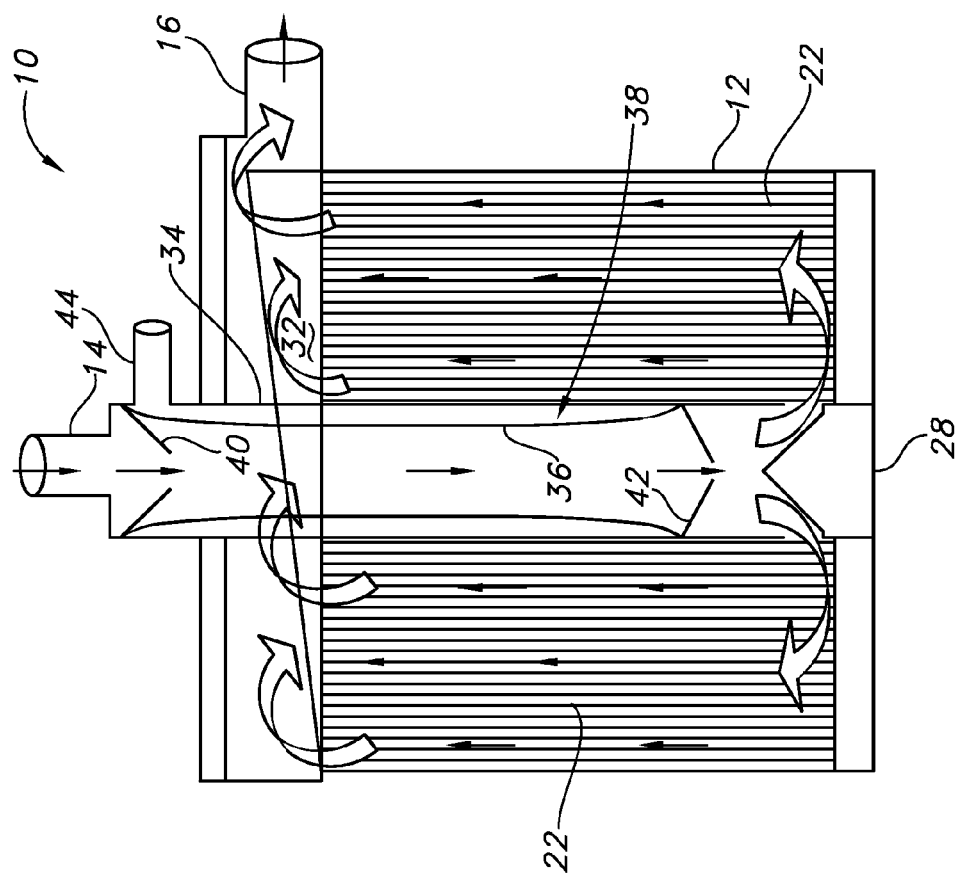
FIG. 7 shows a cross-sectional side view of the oxygenator, including an integrated pneumatic pump.

With reference to FIG. 7, a cylinder 34 is disposed in an interior of the hollow membrane array 22. Within cylinder 34, a flexible membrane 36 is disposed to define a pneumatic pump 38. Pump inlet and outlet valves 40, 42, in an embodiment being duck-bill valves of known configuration, prevent other than a uni-directional blood flow through the pneumatic pump 38 (see arrows).

Figure 8:
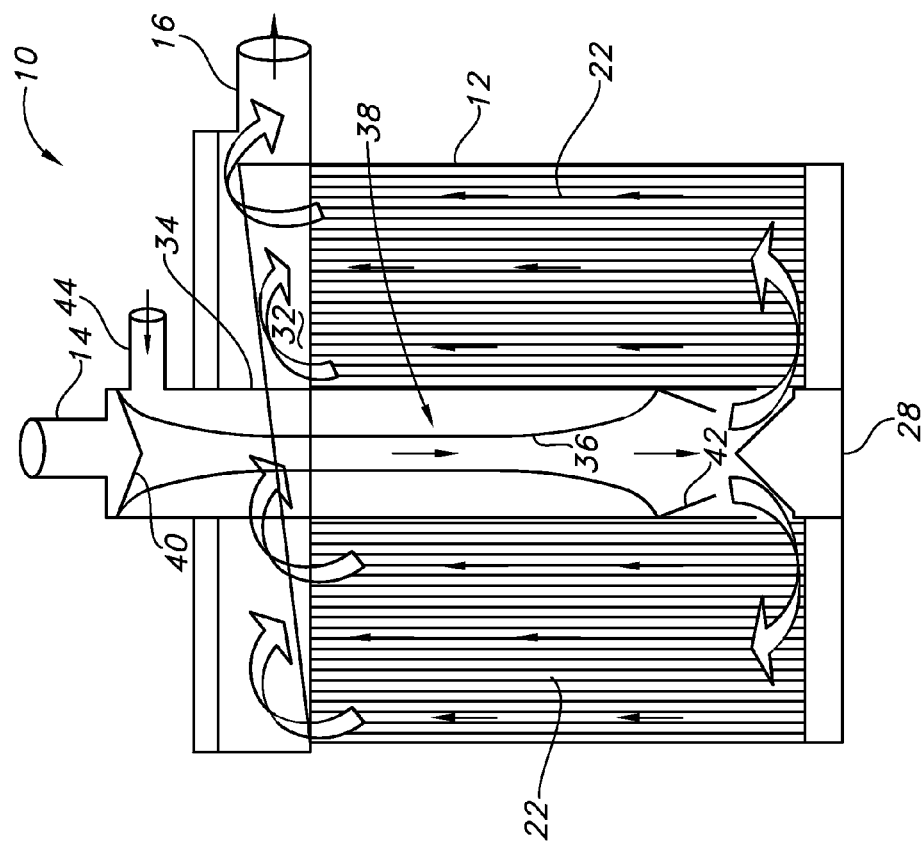
FIG. 8 shows the oxygenator of FIG. 7 in systolic phase.
Figure 9:
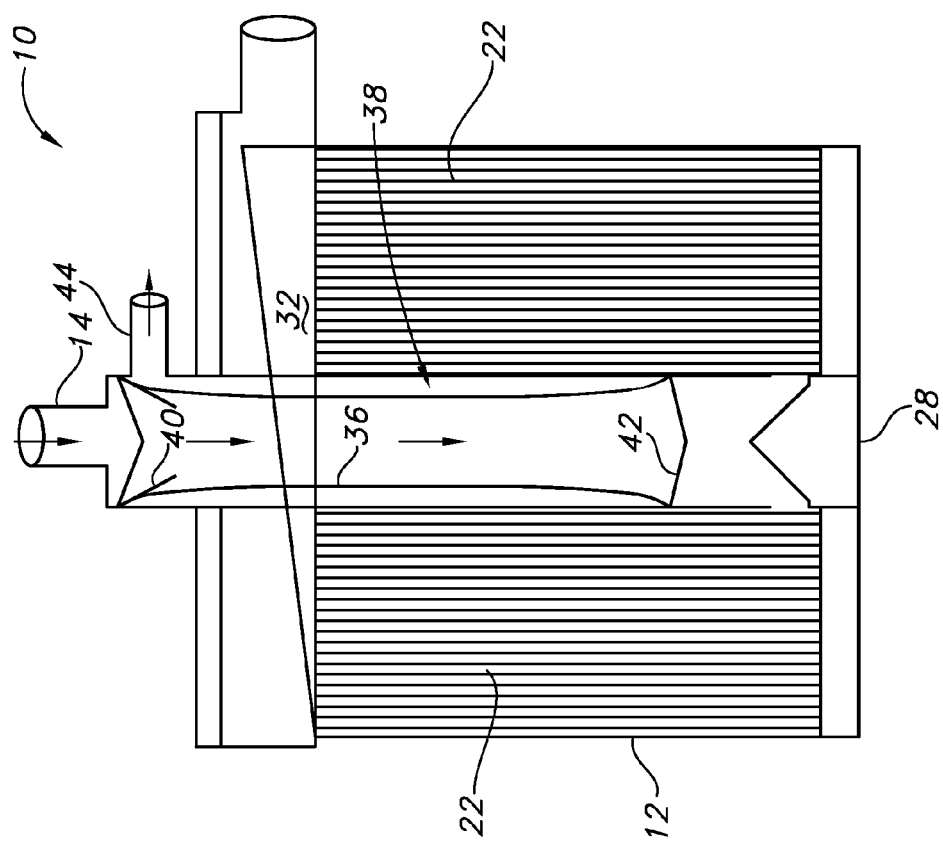
FIG. 9 shows the oxygenator of FIG. 7 in diastolic phase.

A pump gas inlet/outlet 44 is connected to a pneumatic console (not shown) for providing gas to operate the pneumatic pump 38. Pump gas is cyclically supplied to and withdrawn from the pump gas inlet outlet 44, causing the flexible membrane 36 to expand and contract, providing a pumping action to promote blood flow. As shown in FIGS. 8 and 9, when gas is supplied to the pump gas inlet outlet 44 (systole), the flexible membrane 36 collapses, closing the pump inlet valve 40 and forcing blood out of the pneumatic pump 38 via the now open outlet valve 42 to perfuse through the hollow membrane fiber array 22. When gas is withdrawn from the pump gas inlet/outlet 44 (diastole), the flexible membrane 36 expands, closing the pump outlet valve 42 and opening the pump inlet valve 40, generating negative pressure and drawing blood into the pneumatic pump 38 from the patient's body through the now-open pump inlet valve 40. On the next cycle, the blood is delivered from the pneumatic pump 38 as described above.

Figures 10A, 10B:
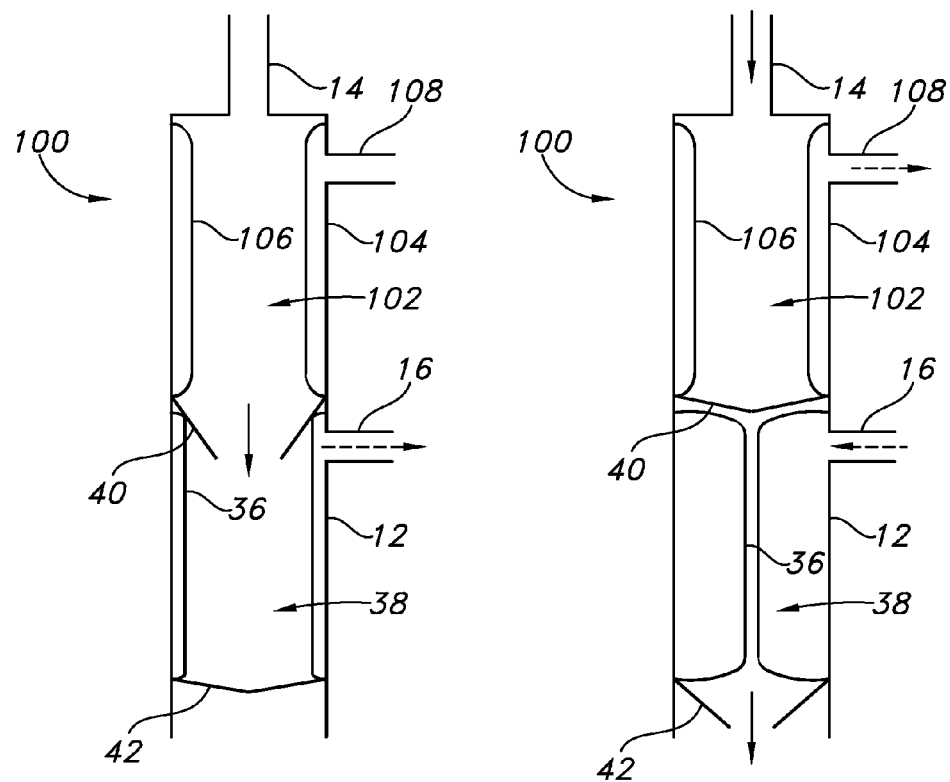
FIGS. 10a and 10b show the oxygenator including an atrium, in diastolic phase (FIG. 10a) and in systolic phase (FIG. 10b)

In another aspect, an atrium 100 is provided which further improves pump performance and blood flow through the oxygenator 10 of the present disclosure (see FIGS. 10a and 10b). In an embodiment, the atrium 100 is defined by at least one additional pneumatic pump 102, disposed at or defining the blood inlet of the oxygenator 10. As shown, the at least one additional pneumatic pump 102 is configured substantially as described above for the integral pneumatic pump 38 of the oxygenator 10, including a pneumatic cylinder 104 and flexible membrane 106, and a gas inlet/outlet 108. For convenience and compactness, the atrium outlet valve may define the inlet valve 40 for the oxygenator 10 integrated pneumatic pump 38, although of course the valve structures may be entirely separate.

The atrium 100 operates in systolic and diastolic phases as described for the oxygenator 10 pneumatic pump 38. That is, cyclically supplying gas to the gas inlet/outlet 108 causes the atrium pneumatic pump 102 flexible membrane 106 to expand and collapse, passing blood through the pneumatic pump 102 and into the oxygenator 10.

In use, the atrium 100 is kept primarily in a state of negative internal pressure by withdrawal of gas, with the exception of a time immediately prior to the diastolic phase of the oxygenator 10 pneumatic pump 38 (see FIG. 11). Typically, the atrium 100 internal pressure is substantially zero at the highest, i.e. during diastole. This is accomplished by intermittently discontinuing withdrawal of gas from the atrium 100 (as distinguished from affirmatively supplying gas to the atrium 100 pneumatic pump 102). In contrast, the oxygenator 10 pneumatic pump 38 is provided only a very short phase of negative internal pump pressure (see FIG. 11). In diastole, when an internal pressure of the atrium 100 pneumatic pump 102 is highest, an internal pressure of the oxygenator 10 pneumatic pump 38 is made slightly negative by withdrawal of gas (see FIG. 11).

By this design, the skilled artisan will appreciate that a consistent flow of blood is established into the inlet of the oxygenator 10 compared to the pulsatile and irregular entry of blood into oxygenators established by conventional designs. This is because the internal pressure of the atrium 100 into which blood first flows is almost always negative and blood is almost always draining from the patient and into the atrium. In turn, very little resistance is imposed to transfer of blood from the atrium 100 into the oxygenator 10 to fill the pneumatic pump 38, since when pump gas is withdrawn from the oxygenator 10 pneumatic pump 38 (diastole, see FIGS. 10a and 11), the internal pressure of the atrium 100 is zero at its highest, i.e. slightly higher than the internal pressure of the oxygenator 10 pneumatic pump 38. By this mechanism, transfer of blood from the atrium 100 to the oxygenator 10 pneumatic pump 38 is promoted by that slight pressure differential. These differentials are shown graphically in FIG. 11. Of course, the more even and non-pulsatile blood flow pattern established between the atrium 100 and the oxygenator 10 achieved by the present mechanism should not be confused with the pulsatile flow established for blood passing through the oxygenator 10 via the oxygenator pneumatic pump 38, for the benefits described above.

The present oxygenator 10 will typically be supplied with blood from a patient's body by a cannula. A dual lumen cannula such as those described in U.S. Pat. No. 7,473,239 and/or U.S. Published Patent Appl. No. US 2011/0040241 is preferred, which both passes blood from a patient's body via a withdrawal cannula into the oxygenator 10 and passes blood back into the patient's body via a delivery cannula. This has the further advantage of reducing the length of the defined blood flow circuit, and eliminates multiple and potentially dangerous (to the patient) cannulations.

There is accordingly provided by the present disclosure an oxygenator 10 which provides a pulsatile, evenly dispersed blood flow therethrough, augmenting gas exchange performance and in turn allowing a lessened gas exchange surface area. The oxygenator 10 may include an atrium 100 defined by one or more additional pneumatic pumps 102, for regulating and providing an even blood supply from a patients' circulatory system into the oxygenator 10. The oxygenator 10 finds use in a variety of procedures, including artificial lung applications and RVAD applications. Unlike conventional oxygenator designs, the present oxygenator 10 reduces or eliminates regions of stagnant or limited blood flow leading to thrombosis and device occlusion failure, and further provides a pulsatile flow which also decreases stagnant blood flow and reduces thrombogenicity.

In turn, the integrated pump design of the oxygenator 10 provides a compact, efficient design which improves patient comfort and mobility, and which also reduces risk of complicating factors such as sepsis and the like resulting from replacing the devices repeatedly. The combined integrated pump/artificial lung design simplifies the PAL circuit in that only one component is provided in the circuit, and further increases pump efficiency by eliminating blood flow resistance from connections between the pump and the artificial lung.

One of ordinary skill in the art will recognize that additional embodiments of the invention are also possible without departing from the teachings herein. This detailed description, and particularly the specific details of the exemplary embodiments, is given primarily for clarity of understanding, and no unnecessary limitations are to be imported, for modifications will become obvious to those skilled in the art upon reading this disclosure and may be made without departing from the spirit or scope of the invention. Relatively apparent modifications, of course, include combining the various features of one or more figures or examples with the features of one or more of other figures or examples.

What is claimed is:

1. A blood oxygenator, comprising:
   a housing, a blood inlet, a blood outlet, a sweep gas inlet, and a sweep gas outlet;
   a hollow membrane fiber array disposed within an interior of the housing for gas exchange to and from blood passing through the oxygenator;
   an inlet blood flow redirector for evenly dispersing blood passing through the blood inlet through a distal end of the oxygenator, the inlet blood flow redirector including a conical tip extending into an interior lumen of a distal end of the blood inlet;
   an outlet blood flow collector for collecting blood exiting the hollow membrane array prior to exiting the oxygenator via the blood outlet; and
   an integrated pneumatic pump disposed substantially within a perimeter defined by the housing, further wherein the integrated pneumatic pump is disposed in an interior of the hollow fiber membrane array.

2. The oxygenator of claim 1, wherein the inlet blood flow redirector defines a substantially frusto-conical shape and is disposed at an end of the housing distal to the blood inlet.

3. The oxygenator of claim 1, wherein the outlet blood collector defines a channel for guiding blood to the blood outlet.

4. The oxygenator of claim 1, wherein the oxygenator pneumatic pump is defined by a cylinder centrally disposed within the hollow membrane fiber array and further including an interior flexible membrane and one or more valves for establishing a unidirectional blood flow by way of a cyclical supply of a pump gas.

5. The oxygenator of claim 4, wherein the valves are unidirectional valves disposed at an entry and at an exit of the flexible membrane for maintaining a unidirectional blood flow.

6. The oxygenator of claim 1, further including another pneumatic pump provided in an atrium disposed at the blood inlet.

7. The oxygenator of claim 6, further including an atrium cyclical gas supply which maintains the atrium at an internal pressure of up to zero.

8. A blood oxygenator, comprising:

a housing, a blood inlet, a blood outlet, a sweep gas inlet, and a sweep gas outlet;

a hollow membrane fiber array disposed within an interior of the housing for gas exchange to and from blood passing through the oxygenator; and an integrated pneumatic pump disposed substantially within a perimeter defined by the housing, further wherein the integrated pneumatic pump is disposed in an interior of the hollow fiber membrane array; and another pneumatic pump provided in an atrium disposed at the blood inlet.

9. The blood oxygenator of claim 8, further including an atrium cyclical gas supply which maintains the atrium at an internal pressure of up to zero.

* * * * *